United States Patent
Sheppard

(10) Patent No.: US 6,712,781 B1
(45) Date of Patent: Mar. 30, 2004

(54) SELF-CONTAINED LIMB AND CAST SUPPORT DEVICE

(76) Inventor: Helen S. Sheppard, RR 2, Box 52, Collins, GA (US) 30421-9544

(*) Notice: Subject to any disclaimer, the term of this patent is extended or adjusted under 35 U.S.C. 154(b) by 52 days.

(21) Appl. No.: 10/146,295

(22) Filed: May 14, 2002

(51) Int. Cl.⁷ .................................................. A61F 5/01
(52) U.S. Cl. ........................... 602/16; 602/23; 602/63; 135/77; 128/845
(58) Field of Search .................... 135/65, 66, 75, 135/77; 128/845; 602/23, 63, 16

(56) References Cited

U.S. PATENT DOCUMENTS

| 3,696,826 | A | * | 10/1972 | Gruzalski | |
| 5,014,690 | A | * | 5/1991 | Hepburn et al. | 602/16 |
| 5,052,379 | A | * | 10/1991 | Airy et al. | 602/16 |
| 5,300,016 | A | * | 4/1994 | Marlatt | |
| 5,318,068 | A | * | 6/1994 | Haugen | |
| 5,547,464 | A | * | 8/1996 | Luttrell et al. | 602/26 |
| 5,575,299 | A | * | 11/1996 | Bieri | |
| 5,735,303 | A | * | 4/1998 | Cole | |
| 5,941,263 | A | * | 8/1999 | Bierman | |
| 6,024,713 | A | * | 2/2000 | Barney | |
| 6,383,156 | B1 | * | 5/2002 | Enzerink et al. | 602/16 |

FOREIGN PATENT DOCUMENTS

FR 2643813 * 9/1990 ............. A61F/5/01

* cited by examiner

Primary Examiner—Robert Canfield
(74) Attorney, Agent, or Firm—John D. Gugliotta

(57) ABSTRACT

A self-contained limb and cast support device that is incorporated into the limb cast upon application of said cast and the second being a self-contained limb and cast support device that is not incorporated into the limb cast for use in instances where the cast is pre-existing or the injured limb requires elevation for healing, but not a cast.

6 Claims, 3 Drawing Sheets

SELF-CONTAINED LIMB AND CAST SUPPORT DEVICE

RELATED APPLICATIONS

The present invention was first described in Disclosure Document Registration filed under 35 U.S.C. §122 and 37 C.F.R. §1.14, but not yet returned. There are no previously filed, nor currently any co-pending applications, anywhere in the world.

BACKGROUND OF THE INVENTION

1. Field of the Invention

The present invention relates generally to medical accessories. More specifically, the present invention relates to a stand used to elevate a broken or sprained limb, whether cast, bandaged or not.

2. Description of the Related Art

Generally, a person wearing a leg or an arm cast due to an operation, bone breakage or fracture, is required to keep his/her leg or arm in an elevated position. It is not always easy to find something to place one's injured leg or arm upon, however. Often in a restaurant situation, a person with a cast needs to ask for an extra chair that because of lack of space underneath the table, needs to be placed in an aisle way causing hassle to restaurant employees and embarrassment to the injured person. Accordingly, a need exists for a portable, space saving stand that can be strapped onto or incorporated with a person's cast. The present invention fulfills this need.

Several attempts have been made to devise a practical cast stand. U.S. Pat. No. 5,318,068 issued to Haugen, discloses a cast support device that can either be built into a crutch or incorporated with a person's cast. The problem with the device disclosed in the '068 Patent, however, is that there is a manual turnstile that the user manipulates in order to raise his/her limb to the proper level. This can prove to be a huge inconvenience for the user and may require another person's help.

A search of the prior art did not disclose any patents that read directly on the claims of the instant invention; however, the following references were considered related. Consequently, the need exists for a cast stand that automatically locks into place and does not require the user to reach the cast stand in order to lock it in place. The present invention fulfills this need.

SUMMARY OF THE INVENTION

It is therefore an object of the present invention to provide an improved cast stand.

It is a feature of the present invention to provide an improved stand used to elevate a broken or sprained limb, whether cast, bandaged or not.

Briefly described according to one embodiment of the present invention, the self-contained limb and cast support device is a self-contained limb and cast support device that is incorporated into the limb cast upon application of said cast and the second being a self-contained limb and cast support device that is not incorporated into the limb cast for use in instances where the cast is preexisting or the injured limb requires elevation for healing, but not a cast.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
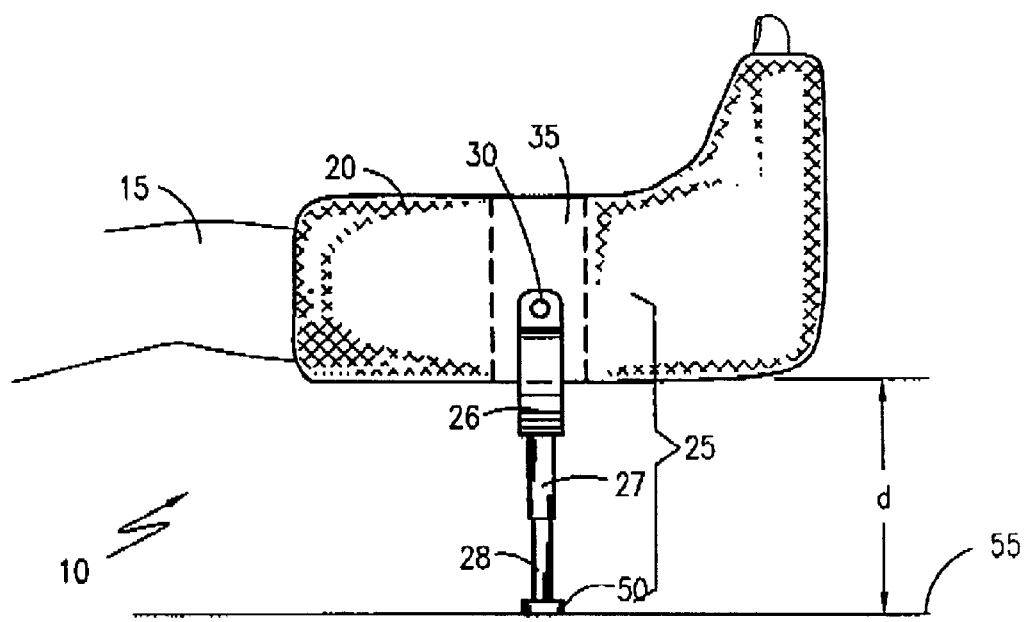
FIG. 1 is a side view of the self-contained limb and cast support device in its deployed state.

The preferred embodiment of the present invention, the self-contained limb and cast support device 10, is shown in FIG. 1. The preferred embodiment of the present invention can be used by anyone in a simple and effortless manner. The self-contained limb and cast support device 10 is generally used to elevate limbs that are broken, strained, sprained, etc. to promote faster healing. A human leg 15 with a cast 20 applied thereto, said cast 20 incorporating the self-contained limb and cast support device 10, is shown in FIG. 1 in a horizontal position as one may find while in a sitting position in a chair. In the preferred embodiment the first strut 25 is pivotally connected at one end thereof to a first connection post 30 that is in turn connected to the internal connection band 35 as shown in FIG. 1. Opposing the first connection post 30 is a second connection post 40 that is connected at one end thereof to the internal connection band 35 and at the opposite end thereof to the second strut 45, a mirror image of the first strut 25. The first and second strut members 25, 45 are pivotally coupled to the first and second connection posts 30, 40 such that the strut members 25, 45 can be turned up to lay against the cast 20 when not being used to elevate said cast 20. It is preferred that both the first and second strut members 25, 45 are telescopic in nature such that the height (d shown in FIG. 1) of each is adjustable for the wearer's sitting position, type of seat, grade conditions, etc. One of ordinary skill in the art would readily recognize that an alternative embodiment of the self-contained limb and cast support device 10 need not have telescoping strut members 25, 45, but rather stationary strut members 25, 45 that are set at a finite height. In this manner, the wearer can utilize the functionality of the self-contained limb and cast support device 10 in multiple seats and seating conditions while following doctors' orders for keeping their limb elevated at all times.

In the preferred embodiment, the first and second strut members 25, 45 are constructed of stainless steel. One of ordinary skill in the art would readily recognize, however, that high-strength plastic or other similar material can be used to construct the first and second strut members 25, 45.

It is preferred that the internal connection band 35 and the connections posts 30, 40 are also constructed of stainless steel. One of ordinary skill the art would readily recognize that high-strength plastic or other similar material can be used to construct the internal connection band 35 and the connections posts 30, 40. It is preferred that the material chosen for construction be slightly pliable so as to mold to the appropriate shape necessary to fit around the limb of the user. In the preferred embodiment, the internal connection band 35, with the connection posts 30, 40 already attached thereto, preferably welded thereto or manufactured as one whole piece, is embedded in the outer layers of the cast 20 during the cast forming process.

After initial wrappings of the cast 20 are applied to the limb, using conventional materials and procedures, the internal connection band 35, with the first and second connection posts 30, 40 coupled thereto on opposing sides thereof, is applied to the partially completed cast and secured in place. Next, the outer wrappings of the cast 20 are completed over the internal connection band 35 leaving only a portions of the first and second connection posts 30, 40 exposed. It is preferred that the remaining components of the self-contained limb and cast support device 10, are applied after sufficient hardening of the cast 20. The self-contained limb and cast support device 10 can be used with all types of casts 20, including older plaster casts as well as newer fiberglass casts.

The preferred embodiment of the self-contained limb and cast support device 10 is adjustable and readily adapts to the various sized legs of human beings from small child through large adult.

In the preferred embodiment, a pair of protective caps 50 are applied to the free ends (the ends thereof that are not connected to the first and second connection posts 30, 40) of both the first and second strut members 25, 45. The protective caps 50 serve two purposes: they protect the floor or ground surface 55 from any possible damage that the strut members 25, 45 may inflict on it, in the case of finished wood floors, sheet vinyl, carpeting or the like and they prevent slippage of the strut members 25, 45 and subsequently the self-contained limb and cast support device 10 along with the human leg 15, in the case of surfaces with a low coefficient of friction such as tile, sheet vinyl, wood floors and the like.

Figure 2:
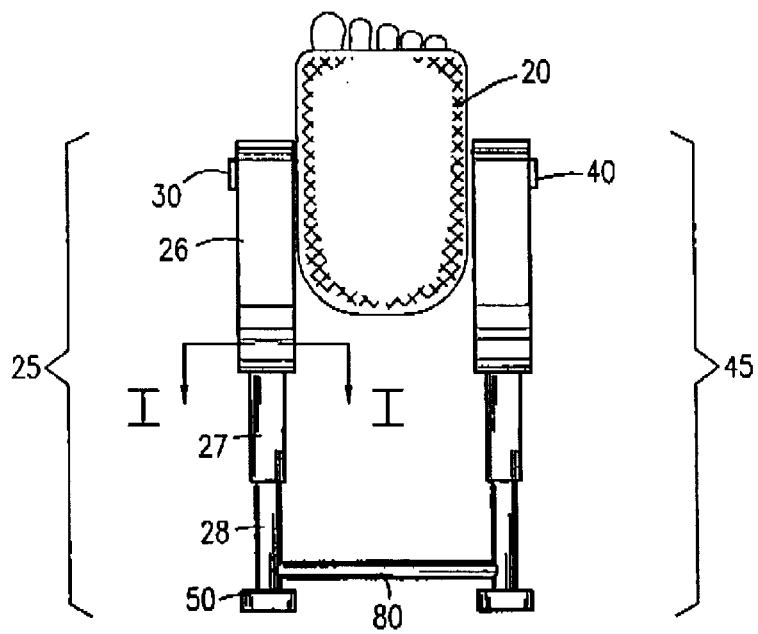
FIG. 2 is a bottom view of the self-contained limb and cast support device in its deployed state.

Referring next to FIG. 2, a bottom view of the self-contained limb and cast support device 10, in its deployed state is depicted in which both the first and second strut members 25, 45 and connection posts 30, 40 can be viewed. Having the first strut 25 directly opposite that of the second strut 45 forms a stable platform such that the wearer's leg will not wobble from side to side. Back and forth motion of the wearer's leg is not hindered by this arrangement, nor should it be, to allow the wearer to move up and down while in a seated position.

As seen in FIG. 2, in the preferred embodiment, the first strut 25 and the second strut 45 are joined together via a cross member 80. The cross member 80 allows the support leg formed by the first strut 25 and the second strut 45 to form a closed stable loop that will not only be more stable for the wearer but remove stress and strain from the first and second connection posts 30, 40.

Figure 3:
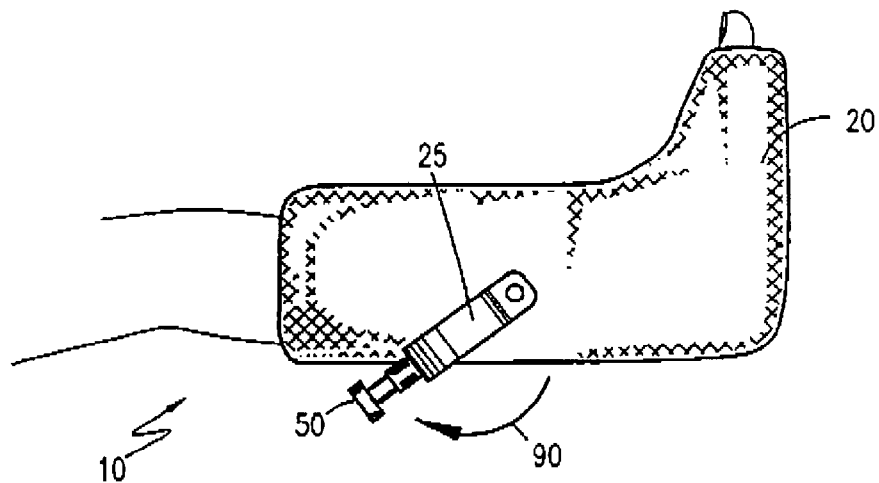
FIG. 3 is a side view of the self-contained limb and cast support device in its retracted state.

The shape of the cross-member 80 can vary. It is preferred that the cross-member 80 is straight in shape for superior strength and support. In an alternative embodiment, the cross-member 80 is slightly "U"-shaped such that when the strut members 25, 45 are turned up, when not in use, the cross-member 80 hugs the shape of the cast 20, see FIG. 3. FIG. 3 illustrates a side view of the self-contained limb and cast support device 10 in its retracted state with the cross-member 80 straight in shape. Both the first and second strut members 25, 45 are retracted and then pivoted up towards the cast 20. This allows the protective caps 50, as well as the cross member 80 to fold up against the cast 20 as shown. This position will not interfere with normal walking, sleeping or lying down. This action is accomplished by releasing the first and second connection posts 30, 40 and rotating the strut members 25, 45 in the direction as defined by a first motion direction arrow 90. This action allows the wearer of the self-contained limb and cast support device 10 to walk about on a walking cast, or to move about with crutches or a wheel chair in a conventional manner, without the self-contained limb and cast support device 10 interfering with mobility. The self-contained limb and cast support device 10 is secured in this retracted position by use of the first and second connection posts 30, 40 that can be tightened and loosened.

Figure 4:
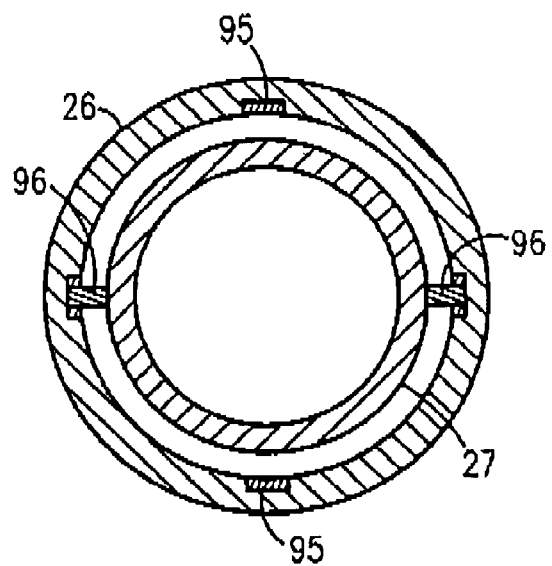
FIG. 4 is a cutaway view of the first upper strut member, taken along a line 1—1, as shown in FIG. 2.

Now referring to FIG. 4, a cutaway view of the first strut 25, taken along a line 1—1 as shown in FIG. 2 is disclosed. In the preferred embodiment, the first strut 25 is composed of three telescoping sections: an upper strut member 26, a middle strut member 27 that slides inside of the upper strut member 26 when retracted and a lower strut member 28 that slides inside of the middle strut member 27 when retracted. A pair of relief slots 95 are provided in the interior portion of each upper and middle strut members 26, 27 at a 180 degree angle to one another. The pair of relief slots 95 provide for the tightening of the lower strut member 28 within the middle strut member 27 and the middle strut member 27 withing the upper strut member 26. To facilitate tightening of said members 26, 27, 28, both the lower member 28 and the middle member 27, have a pair of wings 96 stemming therefrom at a one hundred eighty degree angle from one another, that travel through a pair of channels cut into the interior of each the upper 26 and the middle 27 strut members. To shorten the first strut 25, the lower strut member 28 is twisted until the pair of wings 96 match the pair of channels within the middle strut member 27. The lower strut member 28 is then pushed up into the middle strut member 27 until the wings 96 reach the relief slots 95. At this point, the lower strut member 28 is twisted again, and is thereby locked into place. To lengthen, the same process is repeated until the pair of relief slots 95 at the lower end of the middle strut member 27 are reached and the lower member 28 is again locked into place. The middle strut member 27 adjusts in relation to the upper strut member 26 in the same way as the lower strut member 28 adjusts in relation to the middle strut member 27 as described above. The assembly of the second strut 45 is preferably identical to that of the first strut 25.

Figure 5:
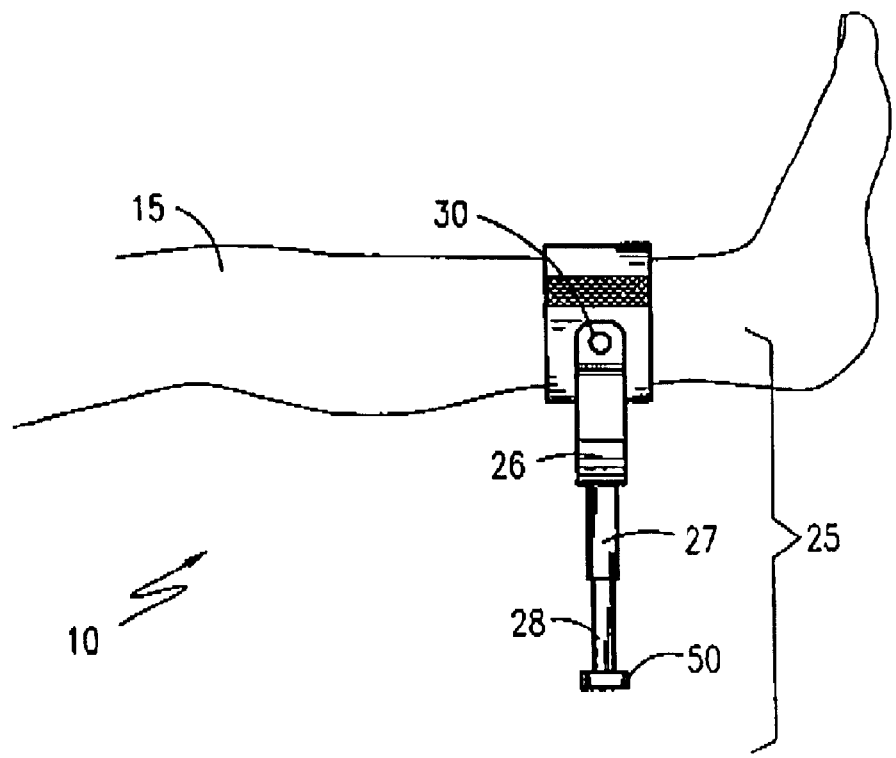
FIG. 5 is a side view of an alternative embodiment of the self-contained limb and cast support device in its deployed state.

An alternate embodiment of the self-contained limb and cast support device 10, is shown in FIG. 5. This embodiment is used in instances where a cast was already applied and the user wants the features of the self-contained limb and cast support device 10 or in instances where the limb injury is a sprain or the like and a cast is not required, but elevation of the affected limb is. In this alternative embodiment, the connection band 35 is external and preferably removable.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A self-contained limb and cast support device comprising:

an internal connection band, embedded within the body of a cast;

a first connection post coupled to one side of the internal connection band such that a portion of said first connection post extrudes the cast;

a second connection post coupled to one side of the internal connection band, opposing said first connection post, such that a portion of said second connection post extrudes the cast;

a first strut rotatably coupled at one end thereof to the first connection post, said first strut having a series of members that are telescopic in nature to one another such that the height of said first strut is adjustable;

a second strut rotatably coupled at one end thereof to the second connection post, said second strut having a series of members that are telescopic in nature to one another such that the height of said second strut is adjustable.

2. The self-contained limb and cast support device of claim 1 further comprising a connecting member for added support, said connecting member having a first end and a second end, the first end thereof coupled to the lowest member of the first strut and the second end thereof coupled to the lowest member of the second strut, such that said connecting member does not interfere with the telescoping nature of the members of the first and second struts.

3. The self-contained limb and cast support device of claim 1 further comprising a pair of protective caps removably coupled to the free ends of the lowest members of said first and second struts.

4. A self-contained limb support device comprising:

an external connection band, sized to fit the circumference of a limb;

a first connection post coupled to one side of the external connection band;

a second connection post coupled to one side of the external connection band, opposing said first connection post;

an first strut rotatably coupled at one end thereof to the first connection post, said first strut having a series of members that are telescopic in nature to one another such that the height of said first strut is adjustable;

a second strut rotatably coupled at one end thereof to the second connection post, said second strut having a series of members that are telescopic in nature to one another such that the height of said second strut is adjustable; wherein said first and second strut each have a free end for supporting the device on a surface.

5. The self-contained limb and cast support device of claim 4 further comprising a connecting member for added support, said connecting member having a first end and a second end, the first end thereof coupled to the lowest member of the first strut and the second end thereof coupled to the lowest member of the second strut, such that said connecting member does not interfere with the telescoping nature of the members of the first and second struts.

6. The self-contained limb and cast support device of claim 4 further comprising a pair of protective caps removably coupled to the free ends of the lowest members of said first and second struts.

* * * * *